United States Patent [19]
Hoyt et al.

[11] Patent Number: 5,925,001
[45] Date of Patent: Jul. 20, 1999

[54] FOOT CONTACT SENSOR SYSTEM

[76] Inventors: Reed W. Hoyt, 23 Willowbrook Rd., Framingham; John F. Lanza, 20 Third St., Matick, both of Mass. 01760

[21] Appl. No.: 08/225,820

[22] Filed: Apr. 11, 1994

[51] Int. Cl.$^6$ .................................................. A61B 5/103
[52] U.S. Cl. ................................................................ 600/595
[58] Field of Search .............................................. 600/595

[56] References Cited

U.S. PATENT DOCUMENTS

| | | | |
|---|---|---|---|
| 3,834,702 | 9/1974 | Bliss | 482/8 X |
| 4,112,728 | 9/1978 | Dutsch | 482/900 X |
| 4,336,933 | 6/1982 | Appelbaum | 482/8 |
| 4,408,183 | 10/1983 | Wills | 482/8 X |
| 4,763,287 | 8/1988 | Gerhaeuser et al. | 482/8 X |
| 4,814,661 | 3/1989 | Ratzlaff et al. | 310/328 |
| 5,200,870 | 4/1993 | Tsuchiya et al. | 482/8 X |
| 5,269,081 | 12/1993 | Gray | 128/779 X |
| 5,323,050 | 6/1994 | Fullen et al. | 128/779 X |

FOREIGN PATENT DOCUMENTS

| | | | |
|---|---|---|---|
| 5161724 | 6/1993 | Japan | 482/8 |
| WO8804768 | 6/1988 | WIPO . | |

OTHER PUBLICATIONS

Kram et al., *Nature*, 346, 265–267 (1990).

*Primary Examiner*—Max Hindenburg
*Attorney, Agent, or Firm*—Henry D. Pahl, Jr.

[57] ABSTRACT

This invention relates to a device and method for determining the metabolic energy expenditure by a human during periods of running or walking. The energy expenditure is correlated with the weight of the subject (W) divided by the time of foot contact with a hard surface (t). This relationship can be programmed into a portable device for the direct measurement of both the rate of energy expenditure and the total energy expended.

20 Claims, 3 Drawing Sheets

FOOT CONTACT SENSOR SYSTEM

BACKGROUND OF THE INVENTION

The present invention relates to a device and method for accurately measuring the amount of metabolic energy expended by an individual during periods of motion, such as walking or running. The device and method of this invention utilize a predictive mathematical relationship to correlate the time of foot contact with a rigid surface, and the weight of the individual, to calculate the metabolic energy expenditure.

Much time and effort in this country and throughout the world is devoted to physical fitness and exercise. The demands for more effective forms of exercise have increased as a result of the time limitations placed on daily activities, and the tendency toward a more sedentary (and less healthy) lifestyle. In addition, issues of individual health are of increasing concern to an aging population. This has led to a search for more efficient methods of exercising, which in turn has spurred the development of increasingly complex and expensive exercise equipment. For example, the use of heart rate monitors for routine exercising is not commonplace. Although the benefits and risks of being physically fit are becoming more apparent, current methods and devices are limited by their unreliability, expense and obtrusiveness.

It is known that most of the force exerted by an individual's muscles acts to oppose gravity, with the average vertical force equal to the total weight of the subject. Thus, the total cost of locomotion, that is the total rate of energy expenditure, varies with body weight and the speed of walking or running. In other words, the metabolic cost of walking and running is primarily determined by the cost of supporting body weight and the rate at which this force is generated.

Existing methods and instruments for measuring metabolic energy expenditure are often imprecise and complex to use. Activity diaries are simple but inherently inaccurate, whereas heart rate monitoring and accelerometry require laborious individual calibration to estimate energy expenditure. Without individual calibration, heart rate estimates of energy expenditure are highly inaccurate, and accelerometry can only be used to differentiate activity from inactivity. Even without individual calibration, heart rate is inaccurate at low activity levels, while the nonlinearity of accelerometer output at high rates of energy expenditure results in significant underestimation of energy expenditure during running.

It has been postulated that the rate of metabolic energy expenditure can be estimated as the total body weight divided by the time during each stride that a single foot is in contact with the ground. As the speed of locomotion increases, foot contact time decreases, and the rate of force generation increases. Thus, a good approximation of the metabolic cost of locomotion may be obtained from measurements of total body weight and foot contact time. This has been demonstrated for non-human animal subjects by Kram et al., *Nature,* 346, 265–267 (1990). Kram et al. concluded that there is a simple inverse relationship between the rate of energy used by an animal for running and the time the foot applies force to the ground during each stride. There is no recognition in Kram et al. as to how this finding could be utilized in a practical manner, or how the finding could be applied to human subjects under conditions of running or walking.

The present invention provides a simplified approach to accurately assess the frequency, duration and intensity of metabolic energy expenditure in humans.

SUMMARY OF THE INVENTION

Figure 1:
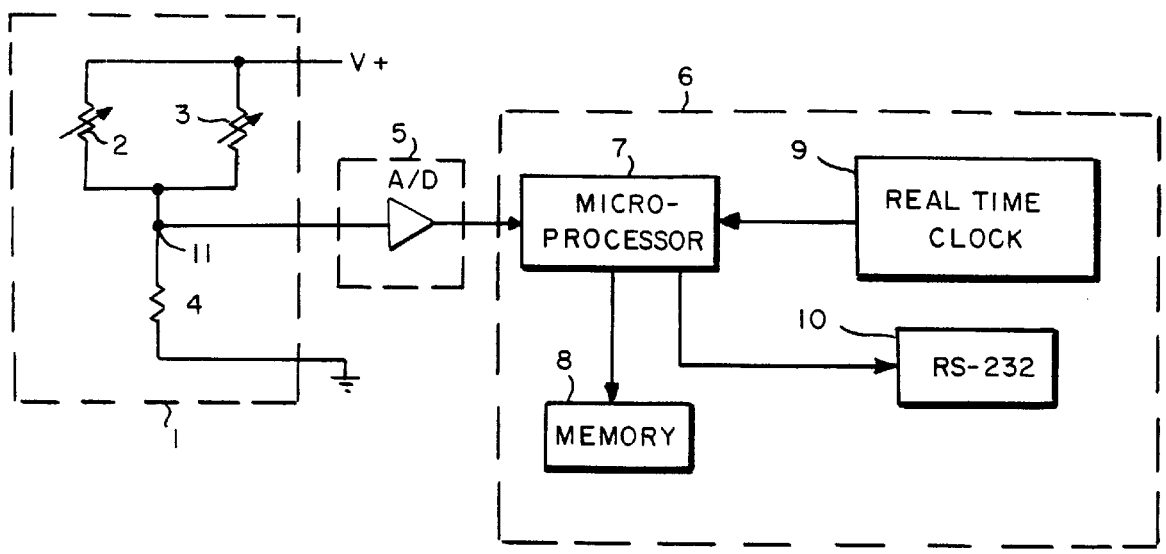
FIG. 1 is a schematic diagram of the electronic components of the ambulatory foot contact monitor.

In accordance with the present invention, a device and method are provided for measuring the metabolic energy expended by an individual during various states of locomotion.

The method of this invention involves measuring the foot contact time (t) of the individual with a hard surface, e.g. the ground or a treadmill, calculation the energy expenditure (E) from the contact time t and the weight of the individual (W), and displaying the result. It has now been determined that the energy expenditure is directly proportional to the individual's weight and inversely proportional to the foot contact time. More particularly, it has been found that these parameters are related according to the following equation:

$$E = A(W/t) + B$$

where A and B are coefficients in the range of about 0.03 and −2.7 respectively, with the energy expenditure expressed in kcal/min and the weight expressed in pounds. This relationship has been found to be applicable to humans during both running and walking.

There are several devices within the scope of this invention which can utilize this relationship in a practical manner. One such device is an ambulatory, electronic foot contact monitor which employs a force sensing resistor as part of a voltage divider circuit to electronically measure the foot contact time. The signal from the voltage divider is transmitted in digital form to a microcontroller, which includes a microprocessor, and the resulting energy expenditure is displayed electronically in a convenient format. This device can be incorporated entirely within a walking or running shoe, if preferred, and can be configured to display both the rate of energy expenditure and the total energy expended during a given time interval.

An alternative device is one which is advantageously incorporated into a stationary exercise platform, either for commercial or home use. In this embodiment, the device can include electronics similar to the electronics used in the ambulatory foot contact monitor, except that an infrared detector is used to record foot contact time by means of reflectors attached to the shoe. The metabolic energy expenditure can be conveniently displayed on a panel for easy viewing by the individual, along with heart rate and other metabolic information.

DETAILED DESCRIPTION OF THE INVENTION

This invention involves a method and device for measuring the metabolic energy expended by an individual during periods of locomotion. The metabolic energy expenditure, designated herein as "E", is the energy expended by an individual human during periods of walking, fast walking, running, or a combination of these states of locomotion.

It has not been found that the metabolic energy expenditure E can be calculated by dividing the weight W of an individual by the foot contact time t with the ground. Specifically, the relationship of E to W and t has been found to be as follows:

$$E=A(W/t)+B \quad (1)$$

wherein A and B are both coefficients which can be expressed in English units or metric units. If expressed in English units, A is in the range of 0.015 to 0.045, preferably about 0.03, and B is in the range of −1 to −4, preferably about −2.7. In metric units, A is in the range of 2.5 to 5.0, preferably about 3.7, and B is in the range of −50 to −300, preferably about −150.

The weight of the individual can also be expressed in pounds or kilograms. As used herein, the term "weight" includes not only the weight of the individual as normally used for physiological purposes, but also any clothing, equipment or load carried by the individual.

The energy expenditure can be calculated and displayed in units or kcal/min, or watts, i.e joules/sec. For the sake of convenience, reference in this application to the foregoing parameters, unless otherwise specifically noted, will be in English units. The total energy expended during a given time period can also be calculated as the product of E and the time interval.

The preferred values of coefficient A and B are 0.03 and −2.7, respectively. It has been found that these values are applicable to the most common conditions of locomotion, such as walking and running. These values may be adjusted within the ranges described shows for mid-range or transition speeds between walking and running. Such adjustments can be made and incorporated in a microprocessor which can be employed to calculate and store the energy expenditure information. Additional adjustments can be made to take into account the effects of sloping or uneven terrain.

Once the foot contact time has been recorded as described below, the energy expenditure can be calculated using suitable electronic processing means, such as a microprocessor. The energy expenditure can then be electronically displayed.

In one embodiment, a device useful in the practice of this invention comprises an ambulatory, electronic foot contact monitor. The monitor includes sensor means for detecting the contact time of a foot as it strikes the ground, means for electronically calculating the energy expended by the individual, based on the foot contact time, the weight of the individual, and predetermined coefficients A and B, and means for displaying the calculated energy expenditure.

The sensor means for detecting the contact time with the ground preferably comprises a force-sensing resistor. A force-sensing resistor which is suitable for use in this invention is one manufactured by Interlink Electronics of Carpenteria, Calif. This resistor is formed from a polymer thin film which exhibits a decrease in resistance with an increase in force applied. The force-sensing resistor is less sensitive to variations in temperature and moisture than piezoelectric sensors used in electronic pedometers. It is also less sensitive to vibration and noise, and significantly less expensive. In addition, the force-sensing resistor measures both the time duration that the foot is up (t') and down (t) during running or walking, and can also record, if desired, the weight of the individual when standing including any equipment worn or carried by the individual. The weight can then be automatically programmed into Equation 1 for calculating the energy expenditure, thereby obviating the need to manually input this data into the device as a separate piece of information.

The force-sensing resistor as described herein can be manufactured in a variety of shapes and forms. For example, the resistor can be shaped to cover the entire insole of a shoe, or only part of the insole. Preferably, a force-sensing resistor is inserted in both the insole and heel portion of the shoe to accurately determine the foot contact time by sensing the downward force of the heel or toe of the user's foot. As used herein, the term "shoe" is intended to include all manner of footwear, such as shoes, boots and sneakers.

Figure 2:
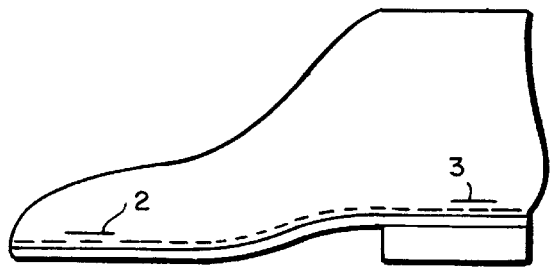
FIG. 2 is a diagrammatic sectional view of a shoe fitted with force-sensing resistors under the insole and heel portions.

Referring now to FIG. 1, force-sensing resistors (2) and (3) are part of sensor circuit (1) located it the bottom of the shoe. Resistor (2) is installed in the bottom of the ball or insole portion of the shoe, and resistor (3) is placed in the bottom of the heel portion of the shoe. This is shown in FIG. 2. Force-sensing resistors (2) and (3) are electrically connected in parallel to each other, and are in turn electrically connected in series with a resistor (4). Resistor (4) is selected to achieve an optimum voltage output at time of foot contact with the ground.

Sensor circuit (1) is essentially a voltage divider circuit. When no force is applied to the foot, the resistances of the force-sensing resistors (2) and (3) are very high, usually in the megohm range, and the voltage at node (11) is near zero. Any force exerted by the user on either force-sensing resistor (2) and (3) will greatly reduce the resistance of the force-sensing resistor, and the voltage at node (11) will dramatically rise and remain at a high level as long as the force is exerted.

The voltage at node (11) is applied to the input of an analog to digital converter (5) which converts this voltage to a proportional digital representation which is then applied to the microprocessor (7).

The microprocessor (7) is part of a microcontroller (6) which also includes memory (8), real time clock (9), and, optionally, a RS-232 serial interface (10). Microprocessor (7) is programmed to sample the output of the digital converter (5) at a fixed rate, for example 100 times per second. This sample is compared to a preset value, for example 20 lbs. If the force exerted on either force-sensing resistor exceeds the binary equivalent of 20 lbs, the microprocessor will decide that the foot is in contact with the ground and will increment as "in contact" counter located in memory (8) by a count of one. The microprocessor will continuously sample the output of the analog to digital converter (5) and increment the "in contact" counter located in memory (8) each time the value exceeds an equivalent of 20 lbs. This will continue until the foot has been raised from the ground causing the voltage produced by the voltage divider circuit (1) to drop to near zero. At this time, the output of the analog to digital converter will output a digital representation of this decreased voltage, and this digital representation will be applied to the microprocessor (7). The microprocessor (7), noting that the output of the analog to digital converter (5) is now less than the equivalent of 20 lbs, will halt the "in contact" counter and record this value in a file in memory (8). The microprocessor (7) continues sampling at 100 samples per second, but each time a sample value is less than an equivalent of 20 lbs a second counter is incremented by one. This counter is the "no contact" counter. This will also continue until the microprocessor (7) senses an input value which is greater than the equivalent of 20 lbs. At this time, the microprocessor will now store the count of the "no contact" counter into a file in memory along with a date/time stamp supplied by the real time clock (9). This process will continue, building a file of three parameters, (a) length of time of foot contact with the ground, (b) length of time the foot is raised, and (c) the real time.

The rate of energy expenditure, as well as the overall energy expended for a given period of time, can be downloaded to a Personal Computer from an RS-232 serial interface (10), or displayed by an electronic display panel (not shown). The electronic display panel can be incorporated in the shoe so as to be visible from the exterior of the shoe through a transparent window. See, for instance, European Patent No. 89340, which describes an electronic pedometer incorporating such a display element. Alternatively, the electronic display can be spaced apart from the electronic calculating and sensing means as described, for instance, in PCT patent publication WO 88/04768. In WO 88/04768, the electronic display means is secured to an upper portion of the shoe so as to be easily visible to the user. This display means is connected to the other electronic circuitry by a flexible lead. The electronic display is typically a digital LED or LCD display.

The electronic circuitry for the sensor and microprocessor can be miniaturized and incorporated into a microchip. This microchip is small enough to be embedded into the insole and heel portion of the shoe. The electronic circuitry also requires a battery which is not shown in FIG. 1. Alternatively, the circuitry can be solar powered in much the same way as an electronic pocket calculator.

The electronic display can be programmed, if desired, to display other parameters of interest such as the speed of travel, the distance traveled, and the elapsed time. The relative speed of the user is calculated from the stride length which can be entered as a separate data input in the same manner as the user's weight.

In another embodiment, the foot contact time can be measured using an infrared detector mounted in proximity to the foot contact surface. For example, an infrared beam emitter can be mounted onto the frame of an exercise treadmill. In this embodiment, the infrared beam is reflected by reflectors attached to the shoe, and the contact time is measured. The electronic components of a circuit for displaying metabolic energy expenditure are the same as described above in connection with the ambulatory monitor. In this embodiment, the electronic display can be incorporated in a raised panel within easy viewing distance of the user. Such an electronic display can also include other metabolic parameters such as heart rate, blood pressure and pulse, to name but a few.

The following examples are intended to further illustrate features of the invention without limiting the scope of the appended claims.

EXAMPLES

Twelve volunteers were used as subjects to assess the accuracy of the portable electronic foot contact time monitor shown in FIGS. 1 and 2 to measure the rate of metabolic energy expenditure during running and walking. The subjects were all healthy males, as determined by physical examination and routine blood and urine tests. The characteristics of the volunteers were as follows: age=19.4±1.4 (SD) yr, height=178±8 cm, and body weight=74.9±7.9 kg. Body weight was measured with a calibrated balance accurate to ±0.05 kg (model 770, Seca, Hamburg, FRG). The subjects were dressed in T-shirts, gym shorts, and running shoes during testing. The 12 volunteers were randomly divided into two equal groups: an equation derivation group and an equation validation group. The two groups did not differ significantly in age, height or weight.

The exercise protocol was identical for both groups. The subjects were tested first during walking (0.89, 1.34 and 1.79 m/s), and then during running (2.46, 2.91 and 3.35 m/s). Treadmill (Quinton Instrument, Seattle, Wash.) grade was 00, and speed was systematically counterbalanced during walking and running. Each bout of exercise was 5 min in duration and separated by a 5- to 10-min rest period. Ambient temperature and relative humidity were about 20° C. and 50%, respectively.

Respiratory gas exchange was measured during the last minute of each exercise bout by an automated open-circuit system that included an infrared $CO_2$ analyzer (Beckman LB-2, Sensor Medics, Yorba Linda, Calif.) and a fuel cell $O_2$ analyzer (Applied Electrochemistry model S-3A, Ametek, Pittsburgh, Pa.) The rate of energy expenditure at each speed during treadmill exercise was calculated from $O_2$ consumption and $CO_2$ production by use of conventional indirect calorimetric relationships. Resting energy expenditure was estimated from height, weight and age by the Harris-Benedict equation. E was calculated by subtracting resting energy expenditure from total energy expenditure.

The time the foot was in contact with the ground t, and the time the foot was in the air t' during each stride were measured with a sensor circuit containing force-sensitive resistors (Force Sensing Resistor, Interlink Electronics, Carpenteria, Calif.) connected to a compact battery-powered programmable ambulatory data logger with 128K of memory (Tattle Tale model IV, Onset Computers, Falmouth, Mass.). The desirable characteristics of the force-sensing resistor include a large decrease in resistance with the application of moderate force; a rapid 1- to 2-ms response time; a wide open temperature range (−20 to 85° C.); resistance to water, oils and acids; very low power requirements (t' current drain less than 10 uA); durability and repeatability ($10^6$ actuations); insensitivity to radio frequency or electromagnetic interference; and relatively low cost.

Referring to FIGS. 1 and 2, two force-sensitive resistors were taped to the bottom of a fitted insole (Poron, Rogers, East Woodstock, Conn.), one under the heel and the other under the ball of the foot. The insole with the force-sensing resistors was placed in the subject's right running shoe. The force-sensing resistors, connected in parallel, were attached in series to a variable 20-kohm resistor and a fixed 5-kohm current-limiting resistor to form a voltage divider-sensor circuit. When 5 V was applied across this circuit, the output voltage varied with the force applied to the force-sensing resistors. During t, sensor circuit resistance decreased dramatically, and the voltage output became more positive. At t', sensor circuit resistance increased and the voltage output became less positive. Sensor circuit output, which was about 3 V during t and about 0.1 V during t', was digitized by an analog-to-digital converter and sampled every 0.01 seconds by the microprocessor. The microprocessor program defined t as a sensor circuit output greater than 2 V and t' as an output less than 1 V.

The data logger's 128K memory was configured as a contiguous block of 8-bit bytes. The binary representation of 0–255 stored in each 8-bit byte was equivalent to 0–2.55 seconds in 0.01-second increments. This was an efficient and accurate method of storing each t or t' value in a single memory byte.

If the sensor circuit voltage exceeded the 2-V set point for t, the microprocessor incremented a memory byte by 1. As long as the t set point was exceeded, this memory byte continued to increment by 1 for every 0.01 second of foot contact. For example, if t was equal to 0.57 seconds, the memory byte was incremented by 1 every 0.01 second for 0.57 seconds, and a binary representation of 57 was stored in the memory. When the microprocessor detected a sensor circuit voltage output less than the t' set point, it immediately started to increment the next contiguous memory byte until the t' set point was exceeded and the microprocessor jumped to the next contiguous byte. This process continued until the test was terminated. At the end of the test, the data stored in memory were downloaded through a standard RS-232 serial interface to a PC-compatible computer. A mean t value for the last minute of each bout of exercise was calculated.

Validity of the equation to estimate E from W/t generated with the derivation group was assessed by the degree of correlation of measured with estimated E across all treadmill speeds for each member of the validation group. Analysis of variance with repeated measures was used to test for significant differences between measured and estimated W and to quantify the variability in estimated and measured W. Individual percent error between estimated and measured W at each walking and running speed was calculated as [(estimated E−measured E)/measured E]×100. The level of statistical significance was set a P less than 0.05. Group $r^2$ and standard error of the estimate (SEE) values were calculated. Values are means ±SD.

Figure 3:
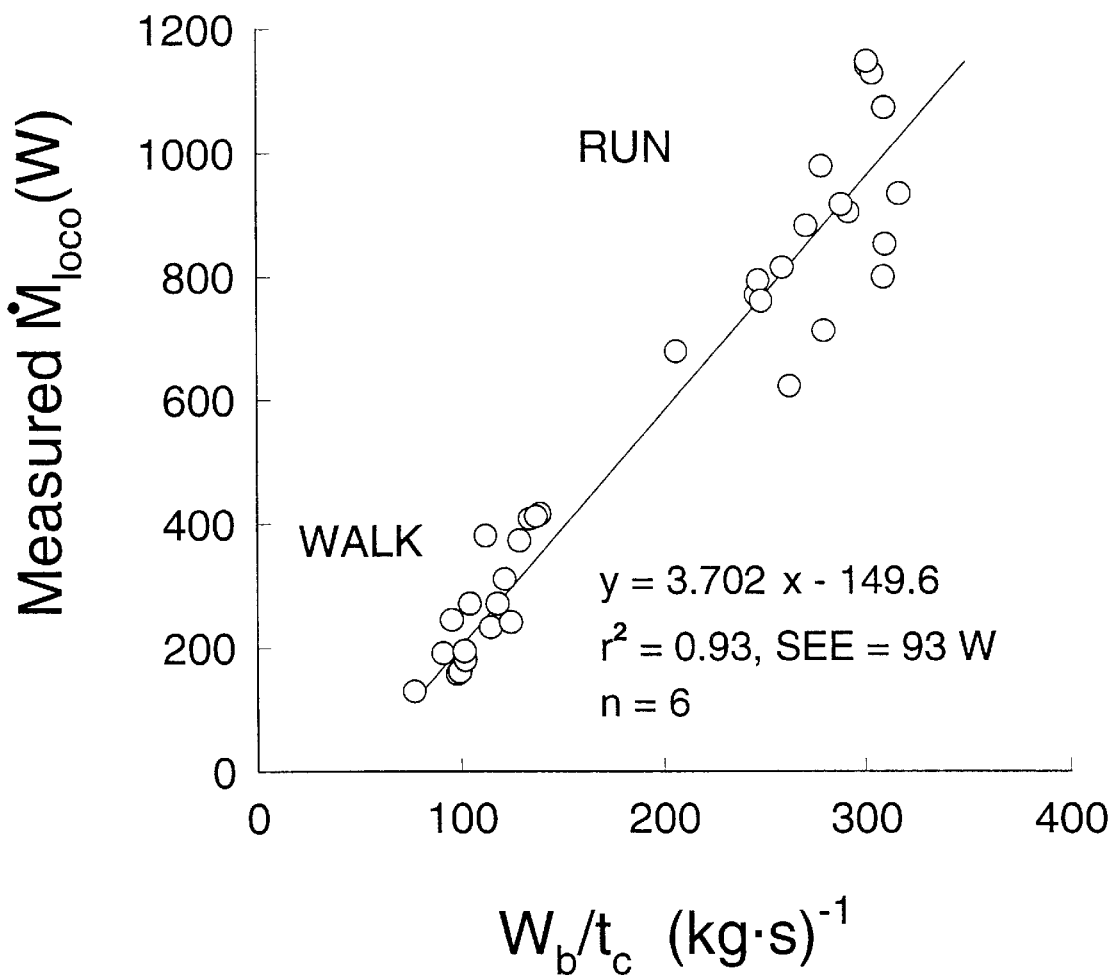
FIG. 3 is a graph showing the relationship of the measured metabolic cost of locomotion to the total body weight divided by the foot contact time for each stride.

The relationship between measured E and W/t (kg/s) is shown in FIG. 3. This relationship was used to derive an equation for estimating the metabolic cost of locomotion $$E = 3.702 \times (W/t) - 149.6 \qquad (2)$$

where $r^2$=0.93 and SEE=93 W

Figure 4:
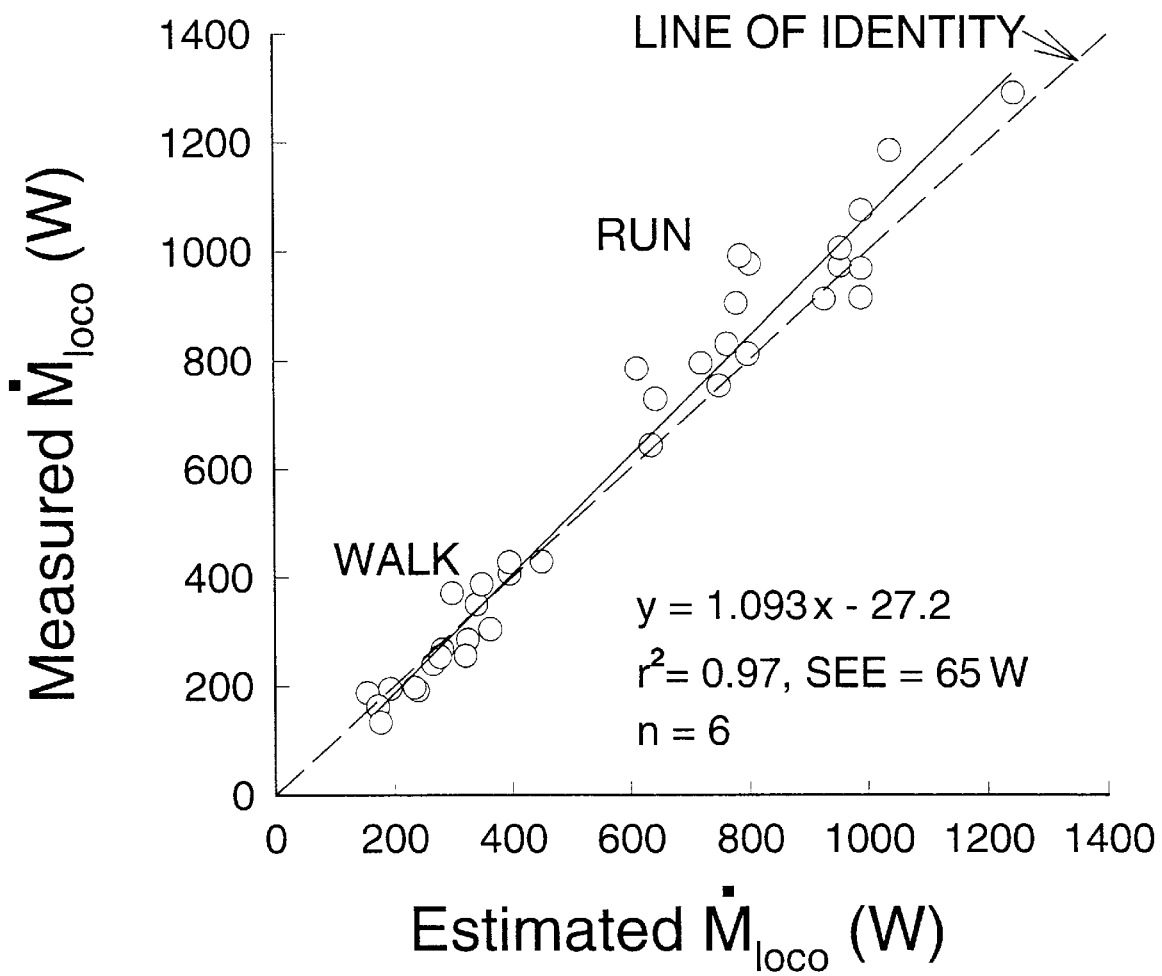
FIG. 4 is a graph showing the relationship of the measured and estimated cost of locomotion.

Equation 2 was independently cross-validated in the second (validation) group by comparing measured E with estimated E calculated from W/t. FIG. 4 shows the close relationship of measured and estimated E. Measured and estimated E were highly correlated ($r^2$=0.97, SEE=65 W), and the regression (measured E=1.093×estimated W−27.2) had a slope close to the line of identity.

Analysis of variance indicated that the measured and estimated E did not differ significantly during walking and/or running. Overall, measured E averaged 599 W and estimated E averaged 573 W, with a mean difference of −26 W. Individual error between measured and estimated E over all six walking and running speeds ranged from −22 to 29% with a mean difference of −0%.

What is claimed is:

1. A method for measuring the energy expended by a human subject during walking or running, said method comprising the steps of:
    a) detecting the contact time (t) of the foot of said human subject against a rigid surface,
    b) calculating the metabolic energy expenditure (E) of said human subject base on the weight of the subject (W) divided by the contact time t, and
    c) electronically displaying the metabolic energy expenditure.

2. The method of claim 1 wherein the energy expenditure is calculated according to the following equation:

$$E = A(W/t) + B$$

where A is a coefficient between 0.015 and 0.045, and B is a coefficient between −1 and −4.

3. The method of claim 2 wherein A is about 0.03 and B is about −2.7.

4. The method of claim 3 wherein said detecting step involves using a sensor incorporated in the heel and toe of a shoe worn by the human subject.

5. The method of claim 4 wherein the energy expenditure is displayed on a portion of the shoe.

6. The method of claim 1 wherein the contact time t is measured using an infrared detector mounted on an exercise platform, said infrared detector recording an infrared beam reflected from a shoe worn by a human subject.

7. A device for measuring the metabolic energy expended by a human subject comprising:
    a) means for measuring the contact time (t) of the foot of a human subject against a rigid surface,
    b) means for calculating the energy expenditure (E) of said human subject based on the weight of the subject (W) divided by the contact time t, and
    c) means for electronically displaying the energy expenditure.

8. The device of claim 7 wherein the energy expenditure E is calculated according to the following equation:

$$E = A(W/t) + B$$

wherein A is a coefficient between 0.015 and 0.045, and B is a coefficient between −1 and −4.

9. The device of claim 8 wherein A is about 0.03 and B is about −2.7.

10. The device of claim 8 wherein said means for measuring includes a sensor incorporated in the heel and toe of a shoe worn by the human subject.

11. The device of claim 10 wherein the sensor comprises a force-sensing resistor incorporate in a voltage divider circuit.

12. The device of claim 11 wherein the sensor further comprises a microprocessor.

13. The device of claim 8 wherein said means for the shoe.

14. The device of claim 8 wherein said means for electronically displaying displays both the amount of energy expended and the rate of energy expenditure.

15. The device of claim 12 wherein the sensor comprises an analog to digital converter which supplies an input voltage to the microprocessor, the microprocessor contains software defining a preset voltage level, and said electronic indicator further comprises a memory which is incremented by one unit for every 0.01 seconds the input voltage exceeds the preset voltage level.

16. A shoe incorporating, as an integral part thereof, the device of claim 7 wherein said means for measuring includes a sensor contained in the heal and toe portions of said shoe.

17. The shoe of claim 16, wherein said shoe includes a transparent window and said means for electronically displaying is placed inside said shoe behind said transparent window.

18. The device of claim 7 wherein the foot contact time t is measured using a detector incorporated in the rigid surface.

19. The device of claim 18 wherein the detector is an infrared detector which records a beam emitted by an infrared source reflected from reflectors attached to the shoe worn by a human subject.

20. The device of claim 19 wherein said means for electronically displaying displays both the amount of energy expended and the rate of energy expenditure.

* * * * *